(12) United States Patent
Simpson (10) Patent No.: US 12,121,221 B2
(45) Date of Patent: Oct. 22, 2024

(54) ILLUMINATION ASSEMBLY FOR HANDHELD MEDICAL DEVICES AND INSTRUMENTS

(71) Applicant: Intersect ENT International GmbH, Hennigsdorf (DE)

(72) Inventor: Kevin Richard Simpson, Austin, TX (US)

(73) Assignee: Fiagon GmbH, Hennigsdorf (DE)

( * ) Notice: Subject to any disclaimer, the term of this patent is extended or adjusted under 35 U.S.C. 154(b) by 428 days.

(21) Appl. No.: 17/680,005

(22) Filed: Feb. 24, 2022

(65) Prior Publication Data
US 2023/0263381 A1 Aug. 24, 2023

(51) Int. Cl.
| | | |
|---|---|---|
| *A61B 1/07* | (2006.01) | |
| *A61B 1/06* | (2006.01) | |
| *A61B 1/227* | (2006.01) | |
| *A61B 1/233* | (2006.01) | |
| *A61M 29/02* | (2006.01) | |

(52) U.S. Cl.
CPC .............. *A61B 1/07* (2013.01); *A61B 1/0684* (2013.01); *A61B 1/227* (2013.01); *A61B 1/233* (2013.01); *A61M 29/02* (2013.01)

(58) Field of Classification Search
CPC ......... A61B 1/07; A61B 1/0684; A61B 1/227; A61B 1/233; A61B 1/00032; A61B 1/00066; A61B 1/00105; A61B 1/0655; A61B 1/12; A61B 1/00082; A61M 29/02
See application file for complete search history.

(56) References Cited

U.S. PATENT DOCUMENTS

| | | | | |
|---|---|---|---|---|
| 5,762,613 A | * | 6/1998 | Sutton | A61B 10/06 600/564 |
| 6,174,307 B1 | * | 1/2001 | Daniel | A61B 1/00098 606/7 |
| 2007/0270788 A1 | * | 11/2007 | Nahen | A61B 1/015 606/15 |
| 2008/0228085 A1 | * | 9/2008 | Jenkins | A61B 1/0008 600/478 |
| 2009/0036744 A1 | * | 2/2009 | Vayser | A61B 1/00135 600/245 |
| 2014/0221740 A1 | * | 8/2014 | Kawula | A61B 1/00016 600/109 |

* cited by examiner

*Primary Examiner* — Mohamed G Gabr
*Assistant Examiner* — Aman Kumar Mann
(74) *Attorney, Agent, or Firm* — Marshall & Melhorn, LLC

(57) ABSTRACT

Described here is an illumination assembly designed to be removably coupled with a variety of other medical instruments, particularly instruments having a tube, channel, or lumen through which a light wire optical fiber can pass through. The illumination assembly has a self-contained power source and is lightweight, allowing for use with a wide variety of instruments. In particular, the present illumination assembly is considered for use with medical device instruments routinely used for ear, nose, and throat (ENT) procedures by otolaryngologists, head and neck surgeons, and other ENT physicians.

20 Claims, 7 Drawing Sheets

ILLUMINATION ASSEMBLY FOR HANDHELD MEDICAL DEVICES AND INSTRUMENTS

RELATED APPLICATIONS

This application is related to Patent Cooperation Treaty ("PCT") application PCT/EP2020/062083, which claims the benefit of priority to U.S. provisional application 62/842,025 filed on May 2, 2019, U.S. provisional application 62/844,922 filed on May 8, 2019, and U.S. provisional application 62/888,631 filed on Aug. 19, 2019, each of which is hereby incorporated by reference in its entirety.

FIELD

This application generally relates to a medical system having a balloon dilation device and an illumination assembly (alternatively referred to as a "light wire" or "light guide") that can couple to the balloon dilation device. The balloon dilation device can be used with various anatomy including tissues of the ear, nose, and throat ("ENT"). The illumination assembly mechanically couples to the balloon dilation device and provides for illumination proximate to the balloon dilation or other functional element of the medical system.

BACKGROUND

Balloon dilation refers to the dilation of a cavity or passageway of a human body with a balloon. Several passageways and cavities in human anatomy can be dilated or expanded using a balloon apparatus, such as the vasculature, paranasal sinuses, the throat, and passageways of the ear (e.g., the ear canal and the Eustachian tube). Conditions where drainage of mucus or fluid from the sinuses or from the ear become blocked can further result in infection. For the sinuses, such infection can develop into a condition called rhinosinusitis. Typically, rhinosinusitis is characterized by symptoms such as nasal discharge, nasal obstruction, facial congestion, facial pain, facial pressure, loss of smell, fever, and headache. Many individuals have chronic rhinosinusitis (CRS), which is generally defined as swelling and inflammation in the sinuses, interfering with the way mucus normally drains, that lasts for three months or longer despite treatment. Chronic sinusitis can be caused by an infection, by growths in the sinuses (e.g., nasal polyps), swelling of the lining of the sinuses, or a combination thereof. Allergic rhinitis (AR), another common paranasal sinus condition, is associated with a group of symptoms affecting the nose that occurs when an individual with the condition breaths in an allergen, such as dust, mold, or animal dander. Allergens cause the release of histamine, which usually causes sneezing, itchy and watery eyes, runny nose, swelling and inflammation of the nasal passages, an increase in mucus production, and for some individuals, hives or other rashes.

Sinusitis can be treated, at least in part, by balloon sinuplasty which involves the positioning of a balloon adjacent to the relevant blockages in the sinus orifices or passages and then dilating (i.e., inflating) the balloon to physically push the blockages outward from the space that is obstructed. The action of positioning the balloon in the correct position requires some form of observation to guide the placement of the device within a patient, where that device is typically handheld by a physician, nurse, or other medical operator. The mechanism of observation can be through navigation (e.g., using one or more sensors on the device in combination with a known mapping of the individual patient anatomy), through illumination (having a light source coupled with the device such that the lit cavity can be seen with an endoscope or other video equipment), or a combination of both. While both navigation and illumination have their benefits, the use of light is a very straightforward approach that does not require additional informational inputs before use.

One of the advantages of a handheld illumination source is that it removes the need for a light source received from capital equipment. Prior implementations of light sources routed onto a balloon dilation device make use of capital equipment that generates the power for the emitted light. Such capital equipment is practically unnecessary for most modern techniques and procedures considered by ENT physicians, where that capital equipment can be unwieldly, takes up a large footprint of space within an office or operating room setting, and is financially an expensive piece of equipment for occasional procedures that in practice only need a relatively modest light source.

Accordingly, there is a need to efficiently provide a light source for such handheld devices, which provides for sufficient illumination for a duration long enough to complete a treatment procedure. Moreover, the light source and the related device will ideally not cause complications to the procedure, which may occur if the light source is a large piece of capital equipment connected to the handheld device, or if the light source is mounted onto the handheld device in a manner that leads the shifting of an element or the weight of the device during a procedure. Such a mobile and modular light source will also be less expensive than capital equipment and have the capability to attach and detach from a wide variety of medical device instruments.

SUMMARY

The present disclosure is directed to a detachable and biocompatible illumination assembly primarily for use with balloon dilation device, where the lighting element of the illumination assembly is structured to extend through the balloon dilation device. In various embodiments, the lighting element can be a filament, a wire, a fiber, an optical guide, or other such conduit for light where that structure can pass through a lumen, tube, channel, or the like of a balloon dilation device, such that the lighting element can extend to and/or past the distal tip of the balloon dilation device. Accordingly, the detachable illumination assembly can be referred to as a "lightwire" or a "lightguide". In application, the illumination assembly can be used to illuminate the treatment area of a subject, particularly tissue surfaces accessible by the balloon dilation device, such as nasolacrimal, otic, nasal, tracheal, or esophageal tissues. Typically, the light emitted from the lightwire coupled to a balloon dilation device provides illumination within the respective body cavity so that a physician or other operator can visually see that body cavity with an endoscope or other optical camera instrument.

It is further contemplated that the detachable illumination assembly can be modular or adaptable, and thus used with medical instruments other than a balloon dilation device. For example, in other ENT applications, a detachable illumination assembly may be of use coupled with other tissue-modifying, tissue-cutting, tissue-ablating, diagnostic, or exploratory instruments, optionally used in combination with an endoscope. In further implementations, the detachable illumination assembly can be used in combination with an electromagnetic navigation system (e.g., for confirmatory visualization).

It should be understood that the device and corresponding systems described herein can be used with a wide range of medical and surgical instruments, and are not limited in application to only ENT treatments. The portable, flexible, and handheld features of the devices described herein lend the device to a wide range of applications or therapies where additional illumination within a body cavity of a patient can be of benefit to use of the operator or physician, improving the functionality of the corresponding system and improving the standard of care for a procedure through increased visual clarity of viewed anatomy.

BRIEF DESCRIPTION OF THE DRAWINGS

Illustrative aspects of the present disclosure are described in detail below with reference to the following drawing figures. It is intended that that embodiments and figures disclosed herein are to be considered illustrative rather than restrictive.

DETAILED DESCRIPTION

Described here is an attachable or auxiliary device, generally referred to as an illumination assembly, for providing illumination to a medical instrument, particularly a medical instrument designed for ENT therapies and procedures. The illumination assembly herein is biocompatible and configured to couple with handheld instruments, providing a lightweight light source for the respective medical instrument to which the illumination assembly couples. In certain applications, the illumination assembly can couple with a dilation balloon device, where the dilation balloon device is designed to dilate passages of cavities within a patient including sinuses, sinus ostia, Eustachian tube passages, and the like.

The illumination assembly described herein employs an optical fiber as the light wire, and the medical device instrument to which the illumination assembly couples is required to have a tube, channel, or lumen through which that optical fiber will pass. Such a tube, channel, or lumen can be anywhere along the length of a subject medical device instrument, but typically that tube, channel, or lumen will have an outlet at the distal end of the medical device instrument such that the optical fiber can emit light and illuminate a working, functional region for that medical device instrument. Accordingly, when deployed within the nose anatomy of a patient, the illumination assembly can be used to locate, illuminate within, and transilluminate across, nasal and sinus structures.

Embodiments of the illumination assembly described here can provide light to the interior of an anatomical cavity having an intensity of from about 0.08 to 1.95 candela (cd). Further embodiments of the illumination assembly can provide light at the intensity set forth above for a duration of at least two hours (2 hr) and up to a duration of about twelve hours (12 hr), and at a minimum, provide light at a sufficient and necessary intensity for the full course of a treatment procedure.

Various medical devices that the illumination assembly can mechanically couple with also include, but are not limited to, sinuplasty balloons. Moreover, for embodiments of the illumination assembly using luer lock internal threads, any medical device or instrument with matching luer lock external threads that directly feeds into a lumen can mechanically couple with the illumination assembly. Accordingly, the illumination assembly can be included as part of the equipment, tools, or system used for various treatments including, but not limited to balloon sinuplasty procedures; any procedure where it is important to identify that a tool is in a frontal or maxillary sinus; and procedures where it is important to locate, illuminate within and transilluminate across nasal and sinus structure.

An illumination assembly as described herein can include: an illumination assembly housing; a battery carriage slidably disposed within the illumination assembly housing, and configured to hold a battery; a fiber coupler connected to a distal end of the battery carriage within the illumination assembly housing; an LED electrically connected to the battery, positioned proximate to the fiber coupler; an optical fiber having a proximal end held by the fiber coupler adjacent to the LED within the illumination assembly housing and having a distal end that extends out of the illumination assembly housing; and a slider casing slidably disposed positioned external to the illumination assembly housing, and mechanically coupled to the battery carriage such that movement of the slider casing is directly translated to movement of the battery carriage. In some aspects, the illumination assembly in the presence of the battery held by the battery carriage, completes an electrical circuit and light is emitted through the light fiber. In other aspects, the illumination assembly further includes a non-conductive element positioned between the LED and the battery carriage that prevents an electrical circuit from being completed. In some implementations, the battery carriage also has a foot spring positioned to exert a force onto an interior track of the illumination assembly housing and thereby prevent uncontrolled movement of the battery carriage within the illumination assembly. In some aspects, illumination assembly is configured to emit light at an intensity of from 0.08 to 1.96 candela. In other aspects, the illumination assembly is configured to emit light for a duration of about two to twelve hours. In further aspects, the slider casing of the illumination assembly is configured to slide a distance of about zero to twenty millimeters. In some implementations, the illumination assembly housing also includes longitudinal passage windows, and the battery carriage further includes tabs configured to fit through the passage windows and mechanically couple with the slider casing. In some aspects, the optical fiber is made of a plastic optical fiber having a diameter of about 0.5 mm and having a numerical aperture (NA) 0.5. In other aspects, the LED emits light at a wavelength ($\lambda$) of from about 618 nm to about 700 nm. In some implementations, the LED is mounted onto a metal core printed circuit board, and the metal core circuit board is mounted onto the battery carriage. In other implementations, the fiber coupler is fit around the LED such that the optical fiber and the LED are in direct contact with each other.

A medical device treatment as described herein can include: (i) an illumination assembly having component parts including: an illumination assembly housing; a battery carriage configured to hold a battery slidably disposed within the illumination assembly housing; a fiber coupler connected to a distal end of the battery carriage within the illumination assembly housing; an LED in electrical communication with the battery forming a circuit; an optical fiber having a proximal end held by the fiber coupler adjacent to the LED within the illumination assembly housing and having a distal end that extends out of the illumination assembly housing; and a slider casing slidably disposed positioned external to the illumination assembly housing, and mechanically coupled to the battery carriage such that movement of the slider casing is directly translated to movement of the battery carriage; and (ii) a medical device instrument configured to treat a medical condition in interior anatomy of a patient, wherein the illumination assembly and the medical device instrument are coupled to each other such that the optical fiber extends through a lumen of the medical device instrument so that the distal end of the optical fiber is proximate to the distal end of the medical device instrument. In some aspects of this medical device treatment system, the optical fiber of the illumination assembly is configured to extend a distance of about 0 mm to 20 mm past the distal end of the medical device instrument. In some implementations, the medical device instrument is configured to treat a frontal sinus, a sphenoid sinus, a maxillary sinus, or an ethmoid sinus of a patient, or a combination thereof. In other implementations, the medical device instrument is configured to treat an auditory anatomy of a patient. In other aspects, the illumination assembly and the medical device instrument when coupled to each other have a balanced and symmetrical weight distribution.

A method of providing light to an interior anatomy of a patient as disclosed herein can include: (i) providing an illumination assembly and providing a medical device instrument, where the illumination assembly and the medical device instrument are configured to mechanically couple with each other, and where the illumination assembly has: an illumination assembly housing which contains therein a slidably disposed battery carriage, a battery held in the battery carriage, a fiber coupler connected to a distal end of the battery carriage, an LED electrically connected to the battery, an optical fiber having a proximal end held by the fiber coupler in a position abutting the LED and having a distal end that extends out of the illumination assembly housing; an electrical connection forming a circuit between the battery and the optical fiber; and a slider casing slidably disposed outside to the illumination assembly housing, mechanically coupled to the battery carriage such that movement of the slider casing is directly translated to movement of the battery carriage; (ii) threading a portion of the optical fiber that extends out of the illumination assembly housing through a channel or lumen of the medical device instrument; (iii) securing the illumination assembly and the medical device instrument to each other; (iv) positioning a distal end of the medical device instrument relative to interior anatomy of a patient; and (v) illuminating the interior anatomy of a patient at a location proximate to the distal end of the medical device instrument. In some implementations, the interior anatomy being treated includes the frontal sinus, the sphenoid sinus, the maxillary sinus, the ethmoid sinus, or combination thereof. In other implementations, the interior anatomy being treated is an auditory anatomy, such as an Eustachian tube.

As used herein, the term "about" when used to modify a numerical value indicates a range of ±10% from the value, unless otherwise explicitly stated.

Figure 1:
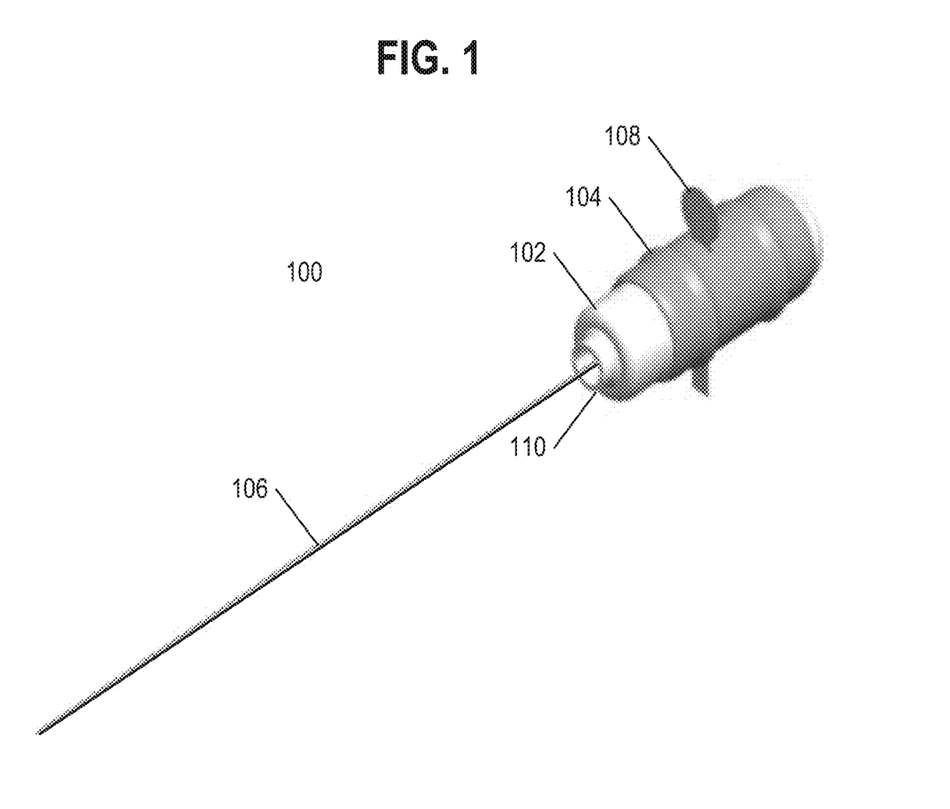
FIG. 1 is a perspective view illustration of an illumination assembly, according to aspects of the disclosure.

FIG. 1 is a perspective view illustration of an illumination assembly 100, viewed independently of a balloon dilation device, having a main body 102 (alternatively referred to as the illumination assembly housing), a slider casing 104, and a light fiber 106 extending from the front end of the main body 102. There is further a pull tab 108 (made of a non-conductive material) inserted into the illumination assembly through respective holes in the main body 102 and the slider casing 104. At the distal end of the main body 102 there is a connection fitting 110 (e.g., a luer lock or luer slip, a pressure-biased fitting, a clamp, a frictional coupler, a twist-to-connect fitting, etc.) that can be configured or adapted to connect the illumination assembly 100 with any given medical instrument having a corresponding connection structure to receive the connection fitting 110.

The pull tab 108 serves a circuit-blocking function for the illumination assembly 100, where there is a battery within the main body 102. When the circuit is complete or uninterrupted, power from the battery causes the light fiber 106 to illuminate. In other words, when the internal circuit of the illumination assembly 100 is complete, light emits from the distal end of the light fiber 106. The pull tab 108 is positioned such that, when present, it interrupts the circuit and blocks the internal circuit from being complete and thus prevents the flow of electricity. Removal of the pull tab 108 from the illumination assembly 100 allows the circuit of the illumination assembly 100 to complete and thus "switch on" to emit light.

Generally, light fiber 106 is a flexible element, capable of fitting through the lumen of another instrument, where such complementary lumens are similarly flexible and required to bend in operation. Further, the flexibility of light fiber 106 allows for the light fiber 106 to be curved or bent to access different anatomy inside a patient. The light fiber 106 can be made from a plastic optical fiber (POF) having a diameter compatible with the lumen through which light fiber 106 needs to pass through. In some embodiments that light fiber 106 diameter (Ø) can be from about 0.2 mm to about 0.8 mm (e.g., 0.5 mm), or at other increments and gradients within that range. In some embodiments, the POF can be a material such as polymethyl-methacrylate (PMMA) or polystyrene resin surrounded by a cladding made of a different polymer or of a silicone resin. In some embodiments, light fiber 106 can be configured to pass and emit light at a wavelength ($\lambda$) of from about 618 nm to about 700 nm. In further embodiments, light fiber 106 can have a numerical aperture (NA) of about 0.5. In further embodiments, light fiber 106 optical core can have a refractive index of from about 1.49 to about 1.59.

Figure 2A:
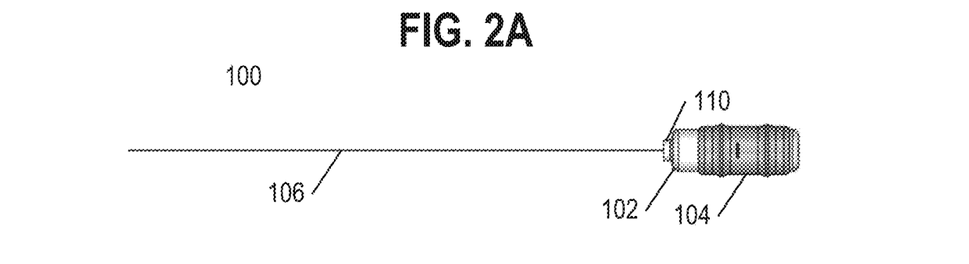
FIG. 2A is a side view illustration of an illumination assembly, according to aspects of the disclosure.

FIG. 2A is a side view illustration of the illumination assembly 100, viewed independently of a balloon dilation device, again showing the main body 102, the slider casing 104, and the light fiber 106 extending out from connection fitting 110 at the front (or distal) end of the main body 102. As shown, the slider casing 104 of the illumination assembly 100 is in a retracted position, biased toward the back (or proximal) end of the main body 102. In other words, when handled by an operator, the retracted position of the slider casing 104 is biased in a direction more proximal to the operator holding the illumination assembly 100.

Figure 2B:
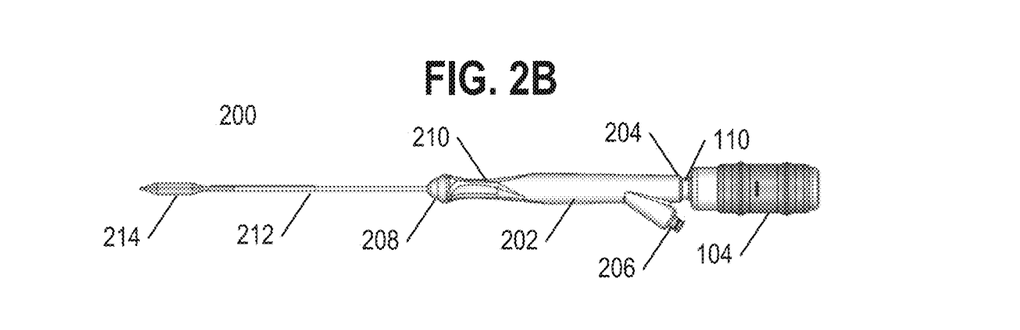
FIG. 2B is a side view illustration of an illumination assembly as in FIG. 2A coupled into a balloon dilation device with the illumination assembly in a retracted position, according to aspects of the disclosure.

FIG. 2B is a side view illustration of an illumination assembly 100 as in FIG. 2A coupled into a balloon dilation device 200 with the slider casing 104 of the illumination assembly 100 in a retracted position biased toward the back of end of the main body 102. Correspondingly, the light fiber 106 is also in a retracted position, fully within the balloon dilation device 200. The balloon dilation device 200 includes a handle body 202, a light source port 204, a fluid port 206, and a handle distal end 208 which is adjacent to an articulated grip surface 210. The balloon dilation device 200 further includes a catheter shaft 212 that extends distally from the handle distal end 208, where the catheter shaft 212 is structured have distinct lumens or channels to allow for the separate passage of fluid or gas (received via the fluid port 206) and the passage of the light fiber 106 from the illumination assembly 100 via the light source port 204. In this position with the light fiber 106 in a retracted position fully within the balloon dilation device 200, a portion of the light fiber 106 is within the handle body 202 and a portion of the light fiber 106 is within the catheter shaft 212. The balloon dilation device 200 further includes a balloon dilator 214 (alternatively referred to as an "expandable" or "inflatable" member or component) positioned at the distal tip of the catheter shaft 212. The balloon dilator 214 is shown here in an expanded state; in an unexpanded or contracted state, the balloon dilator 214 will have an interior diameter commensurate with the outer diameter of the catheter shaft 212. Similarly, the catheter shaft 212 will have a lumen or channel that receives light fiber 106 which has an interior diameter commensurate with the outer diameter of the light fiber 106.

The connection fitting 110 and the light source port 204 are configured to match with and couple to each other, to mechanically secure the illumination assembly 100 to the balloon dilation device 200. The light fiber 106 fits into and through the balloon dilation device 200 via the light source port 204. The light fiber 106 passes through the interior of the handle body 202 and further through the interior diameter of the catheter shaft 212. The length of the light fiber 106, with the slider casing 104 in the retracted position, is long enough to reach the end of the catheter 212 in the region of the balloon dilator 214. In this positional configuration, the light fiber 106 does not extend past the distal tip of the catheter shaft 212. In embodiments of the system and device, when the slider casing 104 is at its rearmost position along the length of the main body 102, the distal end of the light fiber 106 will be aligned with or be at a position slightly within the distal tip of the catheter shaft 212.

The balloon dilator 214 has a fluidic connection to the fluid port 206 that passes through the balloon catheter 212 and the handle body 202. A separate fluid or gas source can be connected to the fluid port 206 in order to deliver fluid or gas to the balloon dilator 214, thereby expanding or inflating the balloon dilator. Following expansion or inflation, that fluid or gas can subsequently be withdrawn via the same fluid port 206, thereby contracting or deflating the balloon dilator.

The articulated grip surface 210 positioned behind the handle distal end 208 is designed to have a shape that is ergonomic for a user, to allow for precise and controlled movement of the balloon dilation device 200 within a patient. As needed, the balloon dilation device 200 can be rotated between the fingers of a user, with the fingers of the use in the region of articulated grip surface 210, without the user losing any substantial control, strength, or positioning of the balloon dilation device 200 within a patient.

Figure 2C:
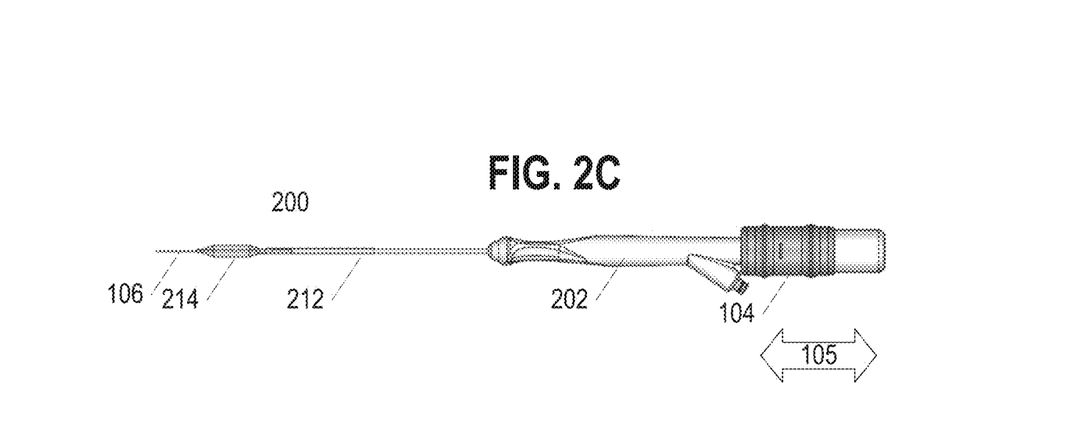
FIG. 2C is a side view illustration of an illumination assembly coupled into a balloon dilation device as in FIG. 2B with the illumination assembly in an extended position, according to aspects of the disclosure.

FIG. 2C is a side view illustration of an illumination assembly 100 coupled into a balloon dilation device 200 as in FIG. 2B with the slider casing 104 of the illumination assembly 100 in an extended (or advanced) position biased toward the front of end of the main body 102. Correspondingly, the light fiber 106 is also in an advanced position, partially extending past the of distal tip of the catheter shaft 212 of the balloon dilation device 200. Arrow 105 illustrates the general range of liner motion of slider casing 104 along the length of main body 102, where in the advanced position slider casing 104 can surround or cover the connection fitting 110 and light source port 204. It should be appreciated that the slider casing 104 in its advanced position may abut but will not physically conflict with or prevent function of any fluid source connected to fluid port 206.

Unlike other illumination-capable devices in the field, the mobile and handheld nature of the illumination assembly 100 when coupled with balloon dilation device 200 allows for the light fiber 106 which extends out from a position in the center of the main body 102, and the illumination assembly 100 itself to be centered along the axis of the balloon dilator 214. Accordingly, because the longitudinal center of rotation of the overall balloon dilation device 200 is around the light fiber 106, the balloon dilation device 200 coupled with the illumination assembly has a balanced and symmetrical weight distribution which improves the ease of use of the overall system. In contrast, devices with an asymmetrical balance of weight, often predicated by the connection to a large capital equipment light source, can be relatively more awkward to use due to the imbalance of weight, in addition to the obstruction of wires connecting to said large capital equipment light source.

The advancement of slider casing 104 leads to a corresponding advancement of the light fiber 106 though the handle body 202 and the catheter shaft 212. This straightforward linear translation means that as the slider casing 104 is moved in either direction (forward or backward) on the main body 102, the light fiber 106 will move an equivalent distance in the corresponding direction. In various embodiments, the range of linear motion of the slider casing can be from zero to fifty millimeters (0 mm-50 mm); accordingly, the distance that the light fiber 106 can extend past the distal tip of the catheter shaft 212 can be from zero to fifty millimeters (0 mm-50 mm). It should be appreciated that the operational range of the light fiber 106 can be any increment or gradient of distance within the range of linear motion described herein. In other embodiments, the functional range of linear motion of the slider casing, and corresponding distance the light fiber 106 can extend past the distal tip of the catheter shaft 212, can be from zero to twenty millimeters (0 mm-20 mm). Similarly, in further embodiments, functional range of linear motion of the slider casing, and corresponding distance the light fiber 106 can extend past the distal tip of the catheter shaft 212, can be from five to twenty millimeters (5 mm-20 mm), from five to twenty-five millimeters (5 mm-25 mm), from ten to twenty millimeters (10 mm-20 mm), from five to fifteen millimeters (5 mm-15 mm), from fifteen to thirty millimeters (15 mm-30 mm), and other analogous spans of distance for the overall range of linear motion. It should be further appreciated that path and range of the slider casing 104 is dependent on the overall length of the main body 102, as the slider casing 104 will remain attached to the main body in both its rearmost and foremost positions.

In some embodiments of the system, either or both of the main body 102 and the handle body 202 can have molding features that provide for haptic feedback to a user sliding the slider casing 104. In other words, a structured bump or divot in the exterior of the main body 102 and/or the handle body 202 can create a tactile resistance which indicates to a user that the slider casing 104 has been moved a specific distance. Similarly, the exterior of either or both of the main body 102 and the handle body 202 can have visual features (e.g., coloring, rings, symbols, combinations thereof, etc.) that provide for visual feedback to a user sliding the slider casing 104. In other words, a visual feature on the exterior of the main body 102 and/or the handle body 202 can indicate to a user that the slider casing 104 has been moved a specific distance. Such tactile or visual features can more specifically indicate that the slider body has been moved an objective distance (e.g., 10 mm, 20 mm, etc.) and/or that the slider body has been moved a predetermined distance specific to a given therapy (e.g., an indicator corresponding to expected deployment within a maxillary sinus, a frontal sinus, a sphenoid sinus, etc.). Embodiments of the system can include both haptic and visual feedback features.

In some embodiments of the system, the light fiber 106 can be rotatable around the longitudinal axis of the device to which the illumination assembly 100 is coupled. Such rotation can be implemented by a rotatable light port (allowing the full illumination assembly 100 to rotate on the back end of the device), or such rotation can be implemented by a rotatable feature built into the illumination assembly 100 itself. The feature to enable such rotation of the light fiber 106 can be a slide, level, or wheel or other such structure on the exterior of the illumination assembly 100.

The illumination provided by the light fiber 106 is generally not dependent on the position of the slider casing 104 or the light fiber 106. Rather, once the circuit for the illumination assembly 100 has been turned on (typically by removing the pull tab 108 which interrupts and prevents the circuit from completing), light will emit from the end of the light fiber 106 regardless of whether the light fiber 106 is positioned at the distal end of the catheter shaft 212 or at any movable position past the distal tip of the catheter shaft 212. The illumination provided through the light fiber 106 can have an intensity of from about 0.08 cd to about 1.96 cd, where the light can be emitted at this range of intensity for a duration of from about two hours to about twelve hours.

Figure 3:
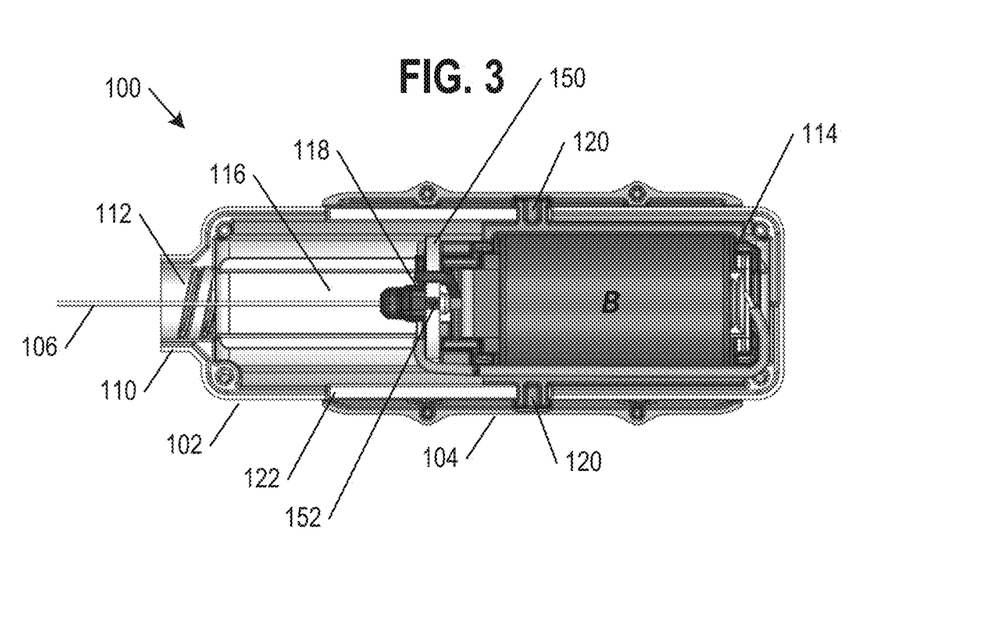
FIG. 3 is a top cross-sectional view illustration of the main body of an illumination assembly, having a battery present, according to aspects of the disclosure.

FIG. 3 is a top cross-sectional illustration view of the main body of an illumination assembly 100, having a battery (B) present, showing components visible on the exterior of the illumination assembly 100, specifically main body 102, slider casing 104, light fiber 106, and connection fitting 110. Further viewable on the interior of illumination assembly 100 in this cross-sectional view are threading 112, battery carriage 114, interior track 116, and fiber coupler 118. Battery carriage 114 is shown here in a retracted or proximal position. The threading 112 on the interior surface of the connection fitting can be manufactured to couple with a wide range of medical devices having various types of light source port 204. In further embodiments, the threading 112 can include structural features to couple with mechanical elements such as luer ports or the like. To secure the illumination assembly 100 to any given medical device with a compatible light source 204, the threading 112 can allow for a rotation ranging from one-half (½) turn to two-whole turns of the illumination assembly 100 to complete the mechanical coupling.

The battery carriage 114 is mostly occluded by battery B in FIG. 3, but the perimeter of battery carriage 114 is shown to encompass the length and diameter of battery B (or width of a non-cylindrical battery) thereby securing battery B within battery carriage 114. Battery carriage 114 is frictionally fit within main body 102, but maintains the freedom to move and be moved along the path of interior track 116. Accordingly, battery carriage 114 will not slide freely within main body 102, but rather only when force is applied by an operator or user to slide battery carriage 114 will battery carriage 114 move along the path of interior track 116. Due to the mechanical connections of tabs 120 (which are part of battery carriage 114) with slider casing 104, where the tabs 120 extend through a passage window 122, force applied to slider casing 104 by an operator or user in a proximal or distal direction directly also moves the battery carriage 114 within the main body 102.

The length of time that the illumination assembly can be used for various functions and treatments (alternatively referred to as the "activation time") naturally relates to the amount of charge held in battery B. Accordingly, a battery B that fits within battery carriage 114 as illustrated will typically be of a size and have a charge sufficient for an activation time of up to twelve hours, or even longer. By extension, in other embodiments of the illumination assembly a smaller battery B can be used to reduce the weight of the overall illumination assembly, which will have a correspondingly shorter duration of activation time. In such embodiments, the minimum activation time the battery B will power and allow for illumination by the illumination assembly is about two hours.

Mounted onto battery carriage 114 is a metal core printed circuit board ("MCPCB") 150 which forms the operational portion of the circuit for the illumination assembly. As the MCPCB 150 is mounting onto the cattery carriage 114, the MCPCB 150 correspondingly slides along with the battery carriage 114 when moved within the main body. The MCPCB 150 can use a variety of metals or metalloids as the substrate for the circuit board, including but not limited to aluminum, silicon, iron, steel, copper, and alloys or combinations thereof. The MCPCB 150 further includes a light emitting diode (LED) 152 that can be mounted onto or into the MCPCB 150 and positioned such that the light emitted by the LED 152 is fit within a corresponding structure of fiber coupler 118 (as described in further detail below). In various embodiments, the LED 152 can be an LED that emits white light, red light, green light, blue light, or another color of visible light as appropriate for viewing internal anatomy. The MCPCB 150, due to its construction having a metal substrate, has the further functionality of operating as a heat sink for thermal energy released by LED 152 or the electrical wires connecting the circuit. This built-in localization of the heat sink prevents thermal energy (or waste heat) from affecting the user or operator handling the illumination assembly 100 during a treatment or procedure. In alternative embodiments, it is of course contemplated that a non-metallic, standard laminate printed circuit board (PCB) having a non-conductive (e.g., fiberglass, epoxy, phenolic, etc.) substrate can be used to couple with the battery carriage 114 and to mount the LED 152.

When the circuit of illumination assembly 100 is complete (i.e., not interrupted by the presence of a pull tab or other functional obstruction), electrical connections (e.g., wires) allow for the controlled flow of electrical current from the battery B to MCPCB 150 and thus LED 152; in other words, these elements form a constant current regulator circuit (CCR). Light fiber 106 is affixed to battery carriage 114 via fiber coupler 118 (shown in further detail in FIG. 7), where the physical connection provided by fiber coupler 118 places light fiber 106 in physical and optical contact with LED 152 such that photons are transmitted from LED 152 into light fiber 106 thereby generating illumination in light fiber 106. In embodiments of the disclosure, a functional obstruction (e.g., pull tab 108) that prevents completion (or breaks) of the circuit is positioned between the MCPCB 150 and the contact with the distal end of a battery B held in battery carriage 114. In other implementations of the illumination assembly 100, a functional obstruction may be positioned at the rearmost or proximal end of the main body 102 interrupting the circuit between an electrical connection and the proximal contact end of a battery B.

Figure 4:
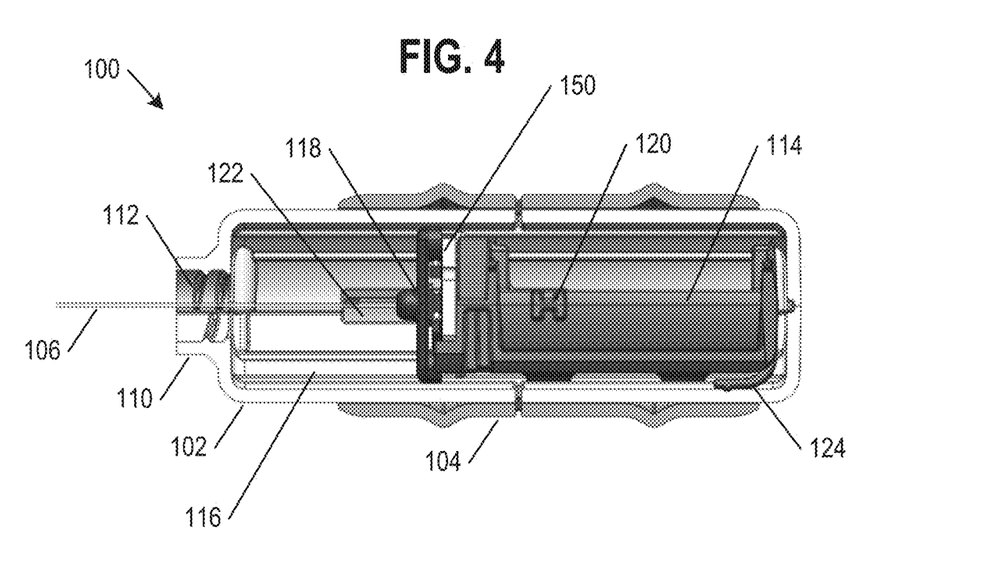
FIG. 4 is a side cross-sectional view of illustration the main body of an illumination assembly (without a battery), according to aspects of the disclosure.

FIG. 4 is a side cross-sectional illustration view of the main body of an illumination assembly (without a battery), in which the interior of illumination assembly 100 is viewable and illustrating threading 112, battery carriage 114, interior track 116, and fiber coupler 118, as well as passage window 122 in which tabs 120 that are a part of battery carriage 114 sit. Also shown is foot spring 124 (alternatively referred to as a "leaf spring") which applies a force onto the interior wall of main body 102, thereby in part providing the frictional fit of battery carriage 114 within the housing. Again, battery carriage 114 is shown here in a retracted or proximal position. Shown here without a battery being held in battery carriage 114, this side cross-sectional illustration shows the alignment of tabs 120 with passage window 122, where the tabs 120 pass through passage window 122 in order to couple with the interior surfaces of slider casing 104. Accordingly, movement of slider casing 104 along the outside of main body 102 leads to corresponding movement of battery carriage 114 on interior track 116, for the given range of motion available within illumination assembly 100.

While the interior track and passage window disclosed herein are linear, it is further contemplated that the movement of a battery carriage and corresponding light fiber could be curved, rotational, or linear, or a combination thereof, in other embodiments of the illumination assembly. Further, while in FIG. 3 and FIG. 4 threading is used within the interior surface of the connection fitting for coupling with a light source port of a medical instrument, it should be appreciated that other mechanical approaches to securing an illumination assembly to a separate medical instrument can be employed, including, but not limited to, a luer lock or luer slip, a pressure-biased fitting, a clamp, a frictional coupler, a twist-to-connect fitting, or the like.

Figure 5A:
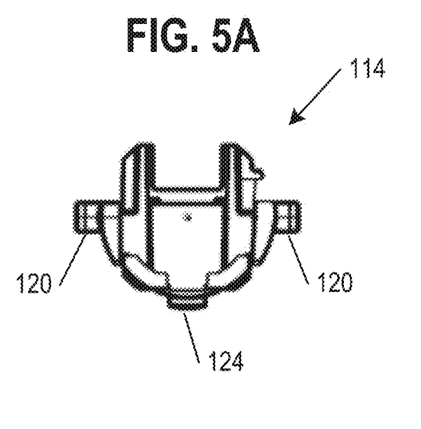
FIGS. 5A, 5B, and 5C are front, side, and bottom perspective schematic views, respectively, of a battery carriage used within an illumination assembly, according to aspects of the present disclosure.
Figure 5B:
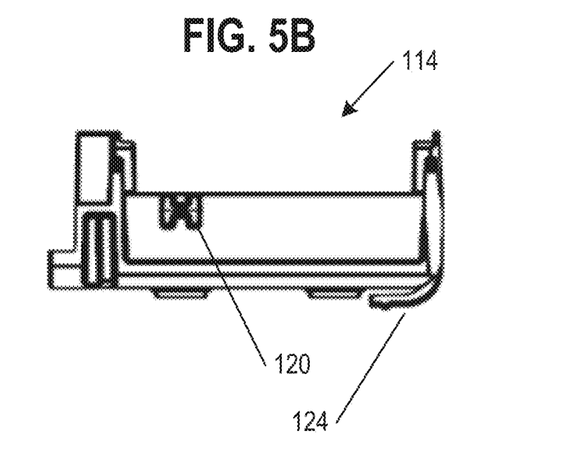
Figure 5C:
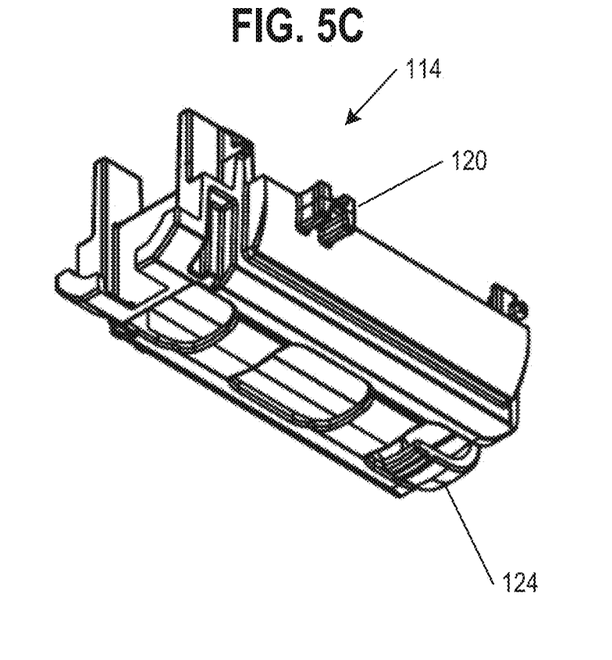

FIGS. 5A, 5B, and 5C are front, side, and bottom perspective schematic views, respectively, of battery carriage 114 used within an illumination assembly, highlighting tabs 120 on the battery carriage 114. Further highlighted is foot spring 124, arranged at the bottom of battery carriage 114. Foot spring 124 applies force onto the interior wall of main body 102, particularly within interior track 116. The force from foot spring 124 frictionally holds battery carriage 114 in place at a position along interior track 116 so that the battery carriage does not shift or slide on its own. In some embodiments (shown in further detail below), there is a groove in the interior wall of main body 102 in the path of interior track 116 where foot spring 124 can reside, acting as a "soft lock" to hold battery carriage 114 in a default proximal position. The frictional force provided by foot spring 124, however is not prohibitive to being moved due to the force applied by an operator or user to slide battery carriage 114 via pushing on slider casing 104. Other aspects of battery carriage 114 include structure at the distal end to receive and couple with a fiber coupler 118, and venting gaps or spaces in the body of battery carriage 114 to avoid overheating of a battery held therein.

Figure 6A:
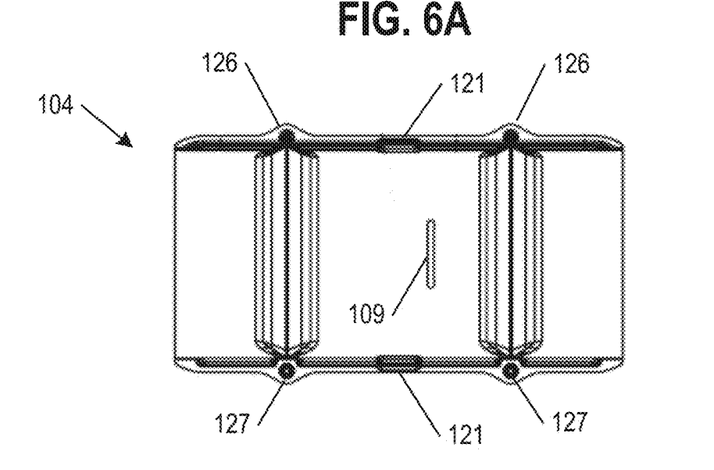
FIGS. 6A, 6B, and 6C are top, side, and perspective schematic views, respectively, of half of a slider casing component, according to aspects of the disclosure.
Figure 6B:
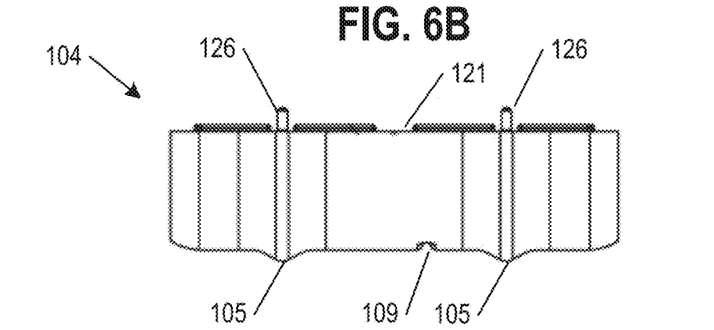
Figure 6C:
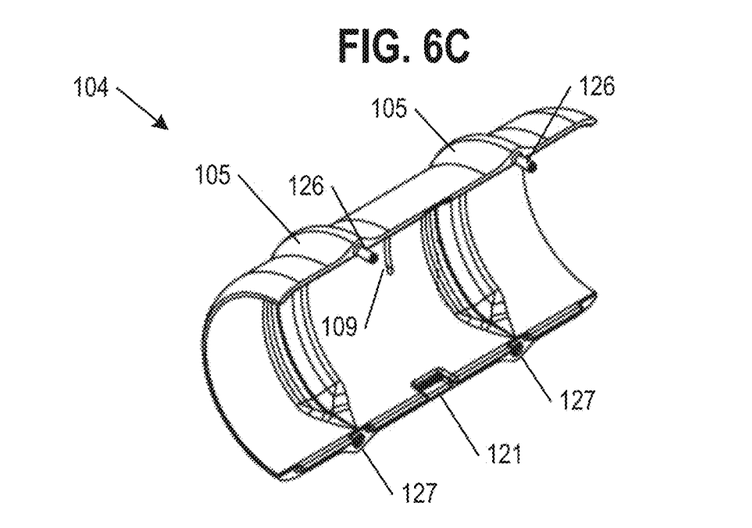

FIGS. 6A, 6B, and 6C are top, side, and perspective schematic views, respectively, of half of a slider casing 104, providing further detail for that component of slider casing 104. Initially, pull tab hole 109 is shown, through which a pull tab 108 as shown above will pass through when in a position to interrupt the circuit of the illumination assembly 100. Similarly, notches 121 are shown on either side ridge of slider casing 104, in which tabs 120 will fit and thereby mechanically couple to a complete slider casing 104. Further illustrated shown are posts 126 and post holes 127, with two posts 126 on one (long) side ridge of the slider casing 104 component, and two post holes 127 on the opposite (long) side ridge of the slider casing 104 component. Accordingly, when two slider casing 104 components as shown are provided, that can be fit together as equal halves where the posts 126 of a first half slider casing 104 fit into the post holes 127 of a second half slider casing 104, and vice versa. The frictional fit between the respective posts 126 and post holes 127 maintain their connection throughout use of the slider casing as part of the illumination assembly 100. The resulting whole slider casing 104 can fit around a main body as shown above, and couple with the tabs 120 of a battery carriage 114 disposed within the main body.

Called out in further detail in FIGS. 6B and 6C are casing ridges 105, which provide a textural or haptic feedback to an operator or user. The casing ridges 105 are a molded feature of slider casing 104, raised up to provide more structural volume for both posts 126 and post holes 127. Casing ridges 105 further provide a physical functionality in that an operator or user holding the illumination assembly 100 does not have to look for a slider or trigger to grip in order to advance the light fiber 106. Rather, due to the fact that the slider casing 104 surrounds the barrel of the main body 102, an operator or user can use their tactile sense to find the casing ridges 105 without need for visual confirmation, and then move (distally or proximally) the slider casing 104. This ergonomic design provides the capability to rely on the sense of touch in order to reposition the light fiber 106 without having to look for a switch or lever in only one location on an instrument is advantageous for performing procedures and treatments efficiently.

Figure 7A:
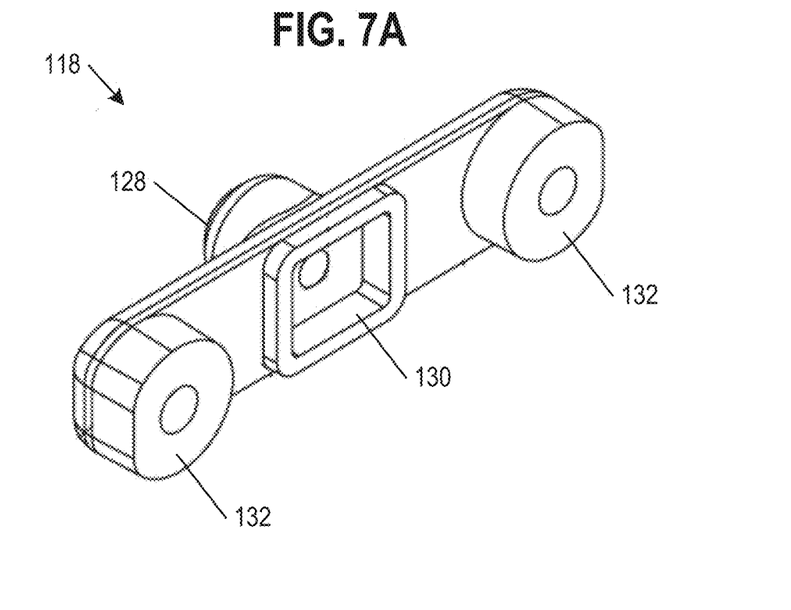
FIGS. 7A and 7B are perspective schematic views of two embodiments a light fiber coupler, according to aspects of the disclosure.

FIG. 7A is a perspective schematic view of a first embodiment of a light fiber coupler 118, illustrating further detail including a fiber receiver 128, a coupler fitting 130 for connecting the fiber coupler 108 to the battery carriage 114, and two standoffs 132 which both maintain a distance for the arrangement of a light fiber 106, electrical connections, and battery carriage 114, as well as providing locations for hardware to mechanically connect the fiber coupler 108 and the battery carriage 114. The fiber receiver 128 is configured to receive an end of light fiber 106, and combination with the coupler fitting 130, abuts and aligns the light fiber 106 with the brightest section of the LED (generally the center of the diode light emitting area, also referred to as the "die"), thereby maximizing the light throughput into the light fiber 106. In some implementations, the light fiber 106, when cut from its source spool of optical fiber, can have the cut end polished to ensure that, once coupled and in contact with the LED 152, the transmissivity of light and that the light emitted at the distal end of light fiber 106 will have the necessary and desired intensity. Further, the coupler fitting 130 is shaped to fit around and over the perimeter of an LED in order to block any light leakage which may otherwise diminish or confuse the light signal provided to the light fiber 106.

Figure 7B:
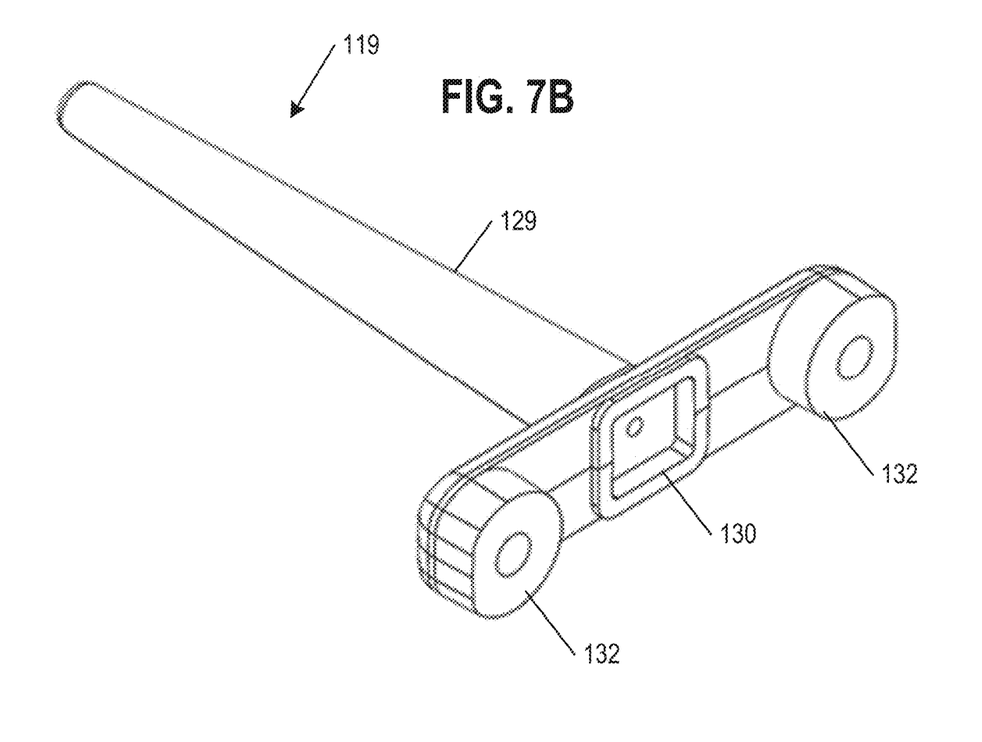

FIG. 7B is a perspective schematic view of a second embodiment of a light fiber coupler 119, illustrating further detail including an extended fiber receiver 129, a coupler fitting 130, and two standoffs 132. In this embodiment, the extended fiber receiver 129 provides for additional mechanical strain relief on the light fiber 106 placed within the extended fiber receiver. Because the light fiber 106 is flexible, it will bend to some degree with the distal end of the light fiber 106 encounters resistance within the anatomy of a patient. The strain relief provided by the extended fiber receiver 129 functions to strengthen the portion of the light fiber 106 within the housing of the main body 102 so that the light fiber 106 does not kink along its length if the distal end of the light fiber 106 pushes up against stiff or resistant anatomy or blockages within a patient.

Figure 8A:
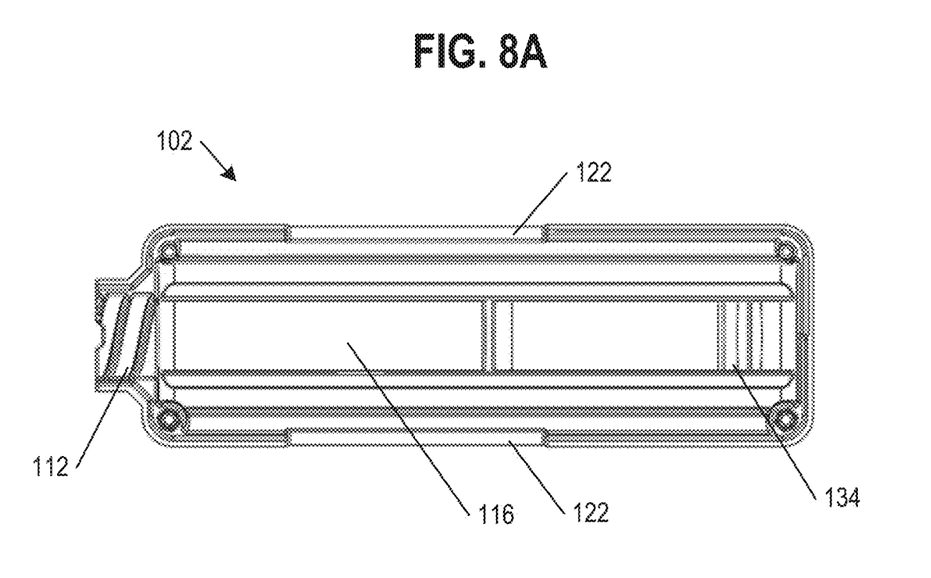
FIG. 8A is a top schematic view and FIG. 8B is a side schematic view of a bottom portion of an illumination assembly housing, according to aspects of the disclosure.
Figure 8B:
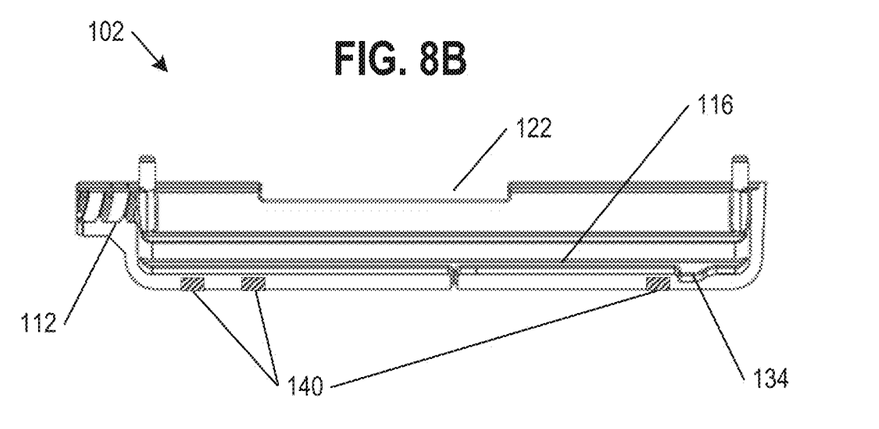

FIG. 8A is a top schematic view and FIG. 8B is a side schematic view of a bottom portion of an illumination assembly housing, in particular a top schematic cross-sectional view of main body 102, showing in isolation threading 112, interior track 116, passage windows 122, and holding groove 134 in the path of interior track 116. The housing for the illumination assembly, and particularly the main body 102, serves a variety of functions. In one aspect, the main body 102 is a protective casing for the functional components, electrical and mechanical, of the illumination assembly 100. In another aspect, the main body 102 prevents light leakage or light escaping, as the main body 102 does not allow for light to escape from its interior and thereby distract an operator or user. Similarly, prevention of light loss through the main body 102 prevents the diminishing or reduction of light signal through the light fiber 106. In a further aspect, the main body 102 serves as an electrical insulator, preventing short circuits or such electrical interruptions in the main body 102 portion of the illumination assembly.

As further seen in FIG. 8B, the exterior of main body 102 can also include markings 140, where such markings 140 are painted, etched, or otherwise imprinted on the external surface of main body 102. Markings 140 are positioned to indicate a distance of movement, such that as slider casing 104 moves along the length of the illumination assembly 100, an operator or user can refer to markings 140 as a quick visual reference to determine the distance the light fiber 106 has been moved. Markings 140 can be positioned on either or both of the distal or proximal end of the main body 102, and can be either covered (not visible) or uncovered (visible) by the slider casing 104 during use. Markings 140 can have a color, pattern, or text as part of their visual appearance. In some embodiments, markings 140 can further have a texture on the exterior of the main body 102 providing a small haptic feedback to an operator or user.

As further seen in FIG. 8B, interior track 116 can have a holding groove 134 positioned at the proximal (or back) end of main body 102, which can be configured to receive a portion of foot spring 124 from battery carriage 114. Accordingly, with foot spring 124 resting partially within the space of holding groove 134, battery carriage 114 will be held in place and will not move along the length of interior track 116 without external forces acting upon it. When an operator or user does apply force (indirectly, through slider casing 104) to battery carriage 114, the placement of foot spring 124 within holding groove 134 will not prevent movement of the battery carriage, but will rather provide haptic feedback to the operator or user that sufficient (or insufficient) force has been applied to slide the battery carriage 114, and by extension the light fiber 106, in a forward and distal direction. Conversely, when withdrawing light fiber 106, the haptic feedback of the foot spring 124 returning into the space of holding groove 134 will indicate to an operator or user that the battery carriage is in a default position and will not move without further application of force. The mechanical resistance between movement of battery carriage 114 when foot spring 124 resides within holding groove 134 will depend in part on the spring coefficient of the foot spring 124.

A straightforward method of use of the illumination assembly described herein can involve the following steps. First, an illumination assembly is provided (typically in an "off" state without the active illumination) alongside a separate medical device instrument, where that separate medical device instrument has a port configured to receive and couple with the illumination assembly. Next, the optical fiber of the illumination assembly into the receiving port and advancing the optical fiber along a tube, channel, or lumen of the medical device instrument until the mechanical connection elements of the illumination assembly and the medical device instrument are in contact or abutting each other. Next, the illumination assembly is coupled to the receiving port of the medical device instrument by the complementary mechanical structures on each component, for example by rotating a male screw structure of the medical device instrument into the threading structure of the illumination assembly. Once connected, the medical device instrument is inserted into the anatomy of a patient to a position where illumination is desired by the operator or user. At the discretion of the operator or user, the illumination assembly is switched "on" such that light is emitted from the illumination assembly. Accordingly, light is emitted at the distal, working, and/or functional end of the medical device instrument to which the illumination assembly is coupled. Also at the discretion of the operator or user, the slider casing on the illumination assembly can be moved to advance or retract the distal end of the optical fiber, where the distal end of the optical fiber can extend a desired or target distance past the distal end of the tube, channel, or lumen of the medical device instrument in which the optical fiber is residing. The light provided by the illumination assembly allows the operator or user to better visualize—and thus better provide treatment—the anatomy around the working or functional component of the medical device instrument.

The devices described herein may be made in any suitable manner. In general, molds may be used to form an illumination assembly designed for specific anatomies or for specific medical devices with which the illumination assembly can couple, and the materials selected for the drug delivery platform may be based on desired compliance for the specific application.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. The term "connected" is to be construed as partly or wholly contained within, attached to, or joined together, even if there is something intervening. Recitation of ranges of values herein are intended to serve as a shorthand method of referring individually to each separate value falling within the range, or gradients thereof, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended to better illuminate embodiments of the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. The invention is susceptible to various modifications and alternative constructions, and certain exemplary embodiments thereof are shown in the drawings and have been described above in detail. Variations of those preferred embodiments, within the spirit of the present invention, may become apparent to those of ordinary skill in the art upon reading the foregoing description. The inventors expect skilled artisans to employ such variations as appropriate, and the inventors intend for the invention to be practiced otherwise than as specifically described herein. Accordingly, it should be understood that there is no intention to limit the invention to the specific form or forms disclosed, but on the contrary, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. An illumination assembly comprising:
   an illumination assembly housing;
   a battery carriage slidably disposed within the illumination assembly housing, and configured to hold a battery;
   a fiber coupler connected to a distal end of the battery carriage within the illumination assembly housing;
   an LED electrically connected to the battery, positioned proximate to the fiber coupler;
   an optical fiber having a proximal end held by the fiber coupler adjacent to the LED within the illumination assembly housing and having a distal end that extends out of the illumination assembly housing; and
   a slider casing slidably disposed positioned external to the illumination assembly housing, and mechanically coupled to the battery carriage such that movement of the slider casing is directly translated to movement of the battery carriage.

2. The illumination assembly of claim 1, where in the presence of the battery held by the battery carriage, an electrical circuit is completed and light is emitted through the light fiber.

3. The illumination assembly of claim 1, further comprising a non-conductive element positioned between the LED and the battery carriage that prevents an electrical circuit from being completed.

4. The illumination assembly of claim 1, wherein the battery carriage further comprises a foot spring positioned to exert a force onto an interior track of the illumination assembly housing and thereby prevent uncontrolled movement of the battery carriage within the illumination assembly.

5. The illumination assembly of claim 1, wherein the illumination assembly is configured to emit light at an intensity of from 0.08 to 1.96 candela.

6. The illumination assembly of claim 1, wherein the illumination assembly is configured to emit light for a duration of about two to twelve hours.

7. The illumination assembly of claim 1, wherein the slider casing is configured to slide a distance of about zero to twenty millimeters.

8. The illumination assembly of claim 1, wherein the illumination assembly housing further comprises longitudinal passage windows, and wherein the battery carriage further comprises tabs configured to fit through the passage windows and mechanically couple with the slider casing.

9. The illumination assembly of claim 1, wherein the optical fiber is comprised of a plastic optical fiber having a diameter of about 0.5 mm and a numerical aperture (NA) 0.5.

10. The illumination assembly of claim 1, wherein the LED emits light at a wavelength ($\lambda$) of from about 618 nm to about 700 nm.

11. The illumination assembly of claim 1, wherein the LED is mounted onto a metal core printed circuit board, and wherein the metal core circuit board is mounted onto the battery carriage.

12. The illumination assembly of claim 1, wherein the fiber coupler is fit around the LED such that the optical fiber and the LED are in direct contact with each other.

13. A medical device treatment system comprising:
   an illumination assembly, comprising:
      an illumination assembly housing;
      a battery carriage configured to hold a battery slidably disposed within the illumination assembly housing;
      a fiber coupler connected to a distal end of the battery carriage within the illumination assembly housing;
      an LED in electrical communication with the battery forming a circuit;
      an optical fiber having a proximal end held by the fiber coupler adjacent to the LED within the illumination assembly housing and having a distal end that extends out of the illumination assembly housing; and
      a slider casing slidably disposed positioned external to the illumination assembly housing, and mechanically coupled to the battery carriage such that movement of the slider casing is directly translated to movement of the battery carriage; and
   a medical device instrument configured to treat a medical condition in interior anatomy of a patient, wherein the illumination assembly and the medical device instrument are coupled to each other such that the optical fiber extends through a lumen of the medical device instrument so that the distal end of the optical fiber is proximate to the distal end of the medical device instrument.

14. The medical device treatment system of claim 13, wherein the optical fiber of the illumination assembly is configured to extend a distance of about 0 mm to 20 mm past the distal end of the medical device instrument.

15. The medical device treatment system of claim 13, wherein the medical device instrument is configured to treat a frontal sinus, a sphenoid sinus, a maxillary sinus, or an ethmoid sinus of a patient, or a combination thereof.

16. The medical device treatment system of claim 13, wherein the medical device instrument is configured to treat an auditory anatomy of a patient.

17. The medical device treatment system of claim 13, wherein with the illumination assembly and the medical device instrument coupled to each other has a balanced and symmetrical weight distribution.

18. A method of providing light to an interior anatomy of a patient, comprising:
- providing an illumination assembly and providing a medical device instrument, where the illumination assembly and the medical device instrument are configured to mechanically couple with each other, wherein the illumination assembly comprises:
  - an illumination assembly housing which contains therein a slidably disposed battery carriage, a battery held in the battery carriage, a fiber coupler connected to a distal end of the battery carriage, an LED electrically connected to the battery, an optical fiber having a proximal end held by the fiber coupler in a position abutting the LED and having a distal end that extends out of the illumination assembly housing; an electrical connection forming a circuit between the battery and the optical fiber; and
  - a slider casing slidably disposed outside to the illumination assembly housing, mechanically coupled to the battery carriage such that movement of the slider casing is directly translated to movement of the battery carriage;
- threading a portion of the optical fiber that extends out of the illumination assembly housing through a channel or lumen of the medical device instrument;
- securing the illumination assembly and the medical device instrument to each other;
- positioning a distal end of the medical device instrument relative to interior anatomy of a patient; and
- illuminating the interior anatomy of a patient at a location proximate to the distal end of the medical device instrument.

19. The method of claim 18, wherein the interior anatomy of a patient is a frontal sinus, sphenoid sinus, maxillary sinus, ethmoid sinus, or combination thereof.

20. The method of claim 18, wherein the interior anatomy of a patient is a Eustachian tube.

* * * * *